(12) United States Patent
Miller

(10) Patent No.: US 7,955,629 B2
(45) Date of Patent: Jun. 7, 2011

(54) METHOD OF FEEDING MILK REPLACER WITH CARNITINE

(75) Inventor: Bill L. Miller, Fort Dodge, IA (US)

(73) Assignee: Land O'Lakes Purina Feed LLC, Arden Hills, MN (US)

( * ) Notice: Subject to any disclaimer, the term of this patent is extended or adjusted under 35 U.S.C. 154(b) by 73 days.

(21) Appl. No.: 12/346,209

(22) Filed: Dec. 30, 2008

(65) Prior Publication Data

US 2009/0326071 A1    Dec. 31, 2009

Related U.S. Application Data

(63) Continuation of application No. 11/036,753, filed on Jan. 14, 2005, now abandoned.

(51) Int. Cl.
*A23K 1/18* (2006.01)

(52) U.S. Cl. ............ 426/2; 426/656; 426/807; 514/561

(58) Field of Classification Search ............. 426/2, 807, 426/656; 514/561
See application file for complete search history.

(56) References Cited

U.S. PATENT DOCUMENTS

| | | |
|---|---|---|
| 5,124,357 A | 6/1992 | Newton et al. |
| 6,242,487 B1 | 6/2001 | Blum et al. |
| 6,303,158 B1 | 10/2001 | Odgaard et al. |
| 6,451,856 B1 | 9/2002 | Blum et al. |
| 7,318,943 B2 | 1/2008 | Baricco et al. |
| 2001/0019724 A1 | 9/2001 | Runge et al. |
| 2003/0165591 A1 | 9/2003 | Baricco et al. |
| 2003/0190404 A1 | 10/2003 | Peisker et al. |

FOREIGN PATENT DOCUMENTS

| | | | |
|---|---|---|---|
| EP | 0484446 B1 | | 5/1995 |
| EP | 0951218 B1 | | 9/2002 |
| RU | 2044493 C1 | * | 9/1995 |
| WO | WO 95/22259 | * | 9/1995 |
| WO | 0048474 A1 | | 8/2000 |
| WO | 0211556 A1 | | 2/2002 |

OTHER PUBLICATIONS

White, T.W. "Influence of L-carnitine on performance and ruminal and blood metabolites of grazing calves and finishing lambs", Professional Animal Scientist, Mar. 2002, 6 pages, downloaded from http://www.google.com/scholar.*

Bonomi , A. "The use of DL-carnitine in weaning calf feeding". Rivista di Scienza dell'Alimentazione, (Gennaio-Marzo, 2000) vol. 29, No. 1, pp. 81-90 (translated document).*

Bonomi, A. et al. "Use of DL-carnitine in the feeding of milk-fed veal calves". Rivista della Societa Italiana di Scienza dell'Alimentazione, (1991) vol. 20, No. 6, pp. 401-416 (translated document).*

* cited by examiner

*Primary Examiner* — C. Sayala

(74) *Attorney, Agent, or Firm* — Dorsey & Whitney LLP; Devan V. Padmanabhan

(57) ABSTRACT

A method of the present invention includes feeding a calf a milk replacer at an enhanced rate with L-carnitine. The method of the present invention enhances weight gain, starter intake and reduces weaning time.

16 Claims, No Drawings

METHOD OF FEEDING MILK REPLACER WITH CARNITINE

CROSS-REFERENCE TO RELATED APPLICATION

The present application is a continuation of U.S. patent application Ser. No. 11/036,753, filed Jan. 14, 2005, now abandoned, the content of which is hereby incorporated by reference in its entirety.

BACKGROUND OF THE INVENTION

The present invention relates generally to a method of feeding a calf and in particular the present invention relates to a method of feeding a calf an enhanced rate of an improved milk replacer containing an effective amount of carnitine.

The feeding of carnitine to heifers, steers and lactating dairy cows is known in the art. PCT Application No. US95/02211, hereinafter the Blum et al application, discloses feeding ruminants such as heifers, steers and lactating dairy cows carnitine either orally or through tubes that discharge directly into the abomasum or rumen. The examples contained in the Blum et al application provided inconclusive or mixed results regarding the effectiveness of feeding heifers, steers and lactating dairy cows carnitine.

The Blum et al application discloses a number of trials including one that was conducted on the effectiveness of feeding carnitine to heifers at a rate of 0.6 grams per day and 1.2 grams per day in a feed consisting of 75 weight percent ground corn and 25 weight percent soybean meal while having access to hay. While average daily gain was statistically significantly greater for the heifers fed the carnitine as compared to the control at the midpoint of the experiment, at the end of the forty two day experiment there was no statistically significant difference in average daily weight gain in the heifers, whether the heifers were fed or were not fed carnitine. Additionally, no significant increase in average daily was recorded when the heifers were fed 1.2 grams of carnitine per day as compared to a rate of 0.6 grams of carnitine per day.

Another experiment was conducted on the effectiveness of feeding carnitine to ten month old steers. Again, the results were inconclusive as to the effectiveness of carnitine. When comparing individual backfat depths after a forty two day trial, the results indicated that steers fed 0.6 grams of carnitine per day had the greatest increase in backfat depth, followed by the steers fed the control without carnitine. The least amount of backfat increase was found in the steers fed the most carnitine, 1.2 grams per day. The results were summarized as being inconclusive because of the high amount of variation in the measurements.

Another experiment provided results on the effect of feeding carnitine to mature ruminally cannulated steers which were also mixed an inconclusive. The results indicated that carnitine supplementation at high levels in a high roughage diet had little effect on nitrogen uptake from the rumen. Acetate to proprionate ratios were not effected by the supplementation of carnitine, although the acetate to proprionate ratios were effected by the time at which the samples were taken.

Additionally, results on the effect of feeding carnitine to lactating dairy cows, either dosed directly into the rumen or the abomasum, were also mixed and inconclusive. Milk production was not affected by dosing carnitine into the rumen or abomasum. Additionally, milk fat content and milk fat yield were decreased when dosed directly into the abomasum. However, carnitine, whether dosed directly into the rumen or abomasum, tended to increase digestible and metabolized energy from the diet which was believed to be directed to body storage.

The Blum et al application speculates that feeding carnitine in a milk replacer would benefit young animals with underdeveloped rumens. However, the Blum et al application does not disclose feeding the milk replacer at enhanced feeding rates that provide higher dosages of carnitine.

SUMMARY OF THE INVENTION

The present invention includes a method of feeding a calf a milk replacer at an enhanced rate with carnitine. The method of the present invention enhances weight gain, starter intake and reduces weaning time in calves. The present invention also includes a method of weaning a calf by feeding the calf a milk replacer at an enhanced rate with carnitine. The present invention also includes a method of accelerating growth of a calf by feeding an enhanced rate of milk replacer with carnitine.

DETAILED DESCRIPTION OF THE PREFERRED EMBODIMENTS

It has been found that when carnitine is added at an effective rate to a milk replacer fed to a calf at the enhanced feeding rate, the calf realizes increases in weight gain, body growth, starter feed intake, and reduces weaning time and electrolyte and medication costs. Carnitine is a natural occurring hydrophilic amino acid derivative of lysine. The carnitine used in the animal feed can be any isomer of carnitine and can be synthetically produced, microbial produced or naturally occurring. Salts of carnitine, such as acetyl carnitine, can also be added to the animal feed.

Under feeding regimens currently employed in the dairy industry, calves are typically fed a fluid milk replacer, at rates that extend up to about 1.25 pounds of the milk replacer on a dry basis per day. Consequently, any feeding rate in this application ranging up to about 1.25 pounds of the milk replacer on a dry basis per day falls within the meaning of the term "conventional feeding rate," as defined herein. Feeding rates of the milk replacer to calves during the pre-weaning period above about 1.25 pounds of the milk replacer on a dry basis per day falls within the meaning of the term "enhanced feeding rate," as defined herein, unless otherwise specified.

Preferably, the enhanced feeding rate for the milk replacer is at least about 1.5 pounds on a dry basis during the pre-weaning period. More preferably, the enhanced feeding rate for the milk replacer on a dry basis is at least about 2.5 pounds per day during the pre-weaning period.

The carnitine is preferably fed at approximately 0.567 grams per day on average at the enhanced feeding rate and preferably at least more than approximately 0.284 grams per day on average. The upper dosage rate of carnitine that produces beneficial results in calves has not yet been determined, however the present application includes dosage rates up to the effective limit of carnitine. The present invention is less effective when usage of carnitine is below 0.284 grams per day on average to calves fed at a conventional feeding rate.

In the specific embodiment described herein, carnitine is fed to a calf as a component of a milk replacer at an enhanced feeding rate to the calf. Preferably, the enhanced feeding rate for the milk replacer is at least about 2.5 pounds of the milk replacer per day based on the dry weight of the milk replacer during the pre-weaning period.

The carnitine is fed to the calf as a component of the milk replacer. The milk replacer includes the animal feed of the present invention such as the milk replacer is made by adding the carnitine into the dry milk replacer. The milk replacer (now containing the carnitine) is then hydrated by the farmer or rancher for feeding to the calf. Alternatively, the milk replacer can be hydrated and then the carnitine may be added to the hydrated milk replacer.

The method of the present invention is described in the following examples. These examples are provided as an illustration of the invention and is not intended to limit the invention in any way.

Example 1

A total of 33 calves were provided with the milk replacer of the present invention at an enhanced feeding rate. Seventeen of the calves were fed milk replacer without carnitine and the other sixteen calves were fed milk replacer with carnitine. Both groups of calves were fed the same amount of the milk replacer at an enhanced feeding rate where the calves were fed about 1.80 pounds of milk replacer per day in two feedings during days 1-7, about 2.5 pounds of a milk replacer per day in two feedings during days 8 through 42 and 1.25 pounds of milk replacer per day during one feeding during days 43-49 of the trial where the weight of the milk replacer is presented on a dry basis. During days 1-7 of the trial the sixteen calves received 205 mg/head/feeding of carnitine and during days 8-49 of the trial the calves received 284 mg/head/feeding. Both groups of calves were provided a starter feed that was consumed ad libitum.

The carnitine used in these trials was L-Carnitine purchased from North American Ingredients, Inc. of Marion, Tex. The calf milk replacer (CMR) used was Cow's Match™ from Land O'Lakes, Inc. of Arden Hills, Minn. The results from the trials were combined and are set forth below in Tables 1 through 6. The procedures followed in the four trials were similar.

The calves used in the trials were approximately 3 to 10 days old at the trial's initiation. Each calf was weighed initially upon arrival and weekly thereafter. Other performance parameters were also determined on a weekly basis.

As Table 1 set forth below indicates, a statistically significant gain in weight occurred in the calves in periods 3, 7 and overall. The total weight gain for the seven periods for calves fed the Cow's Match™ CMR with carnitine showed approximately 21% greater increase over the calves fed Cow's Match™ CMR at the enhanced feeding rate without carnitine.

There was also a significantly greater starter intake by the calves fed the Cow's Match™ CMR with carnitine in periods 6 and 7. Total starter intake by calves fed the Cow's Match™ CMR with carnitine was approximately 34% greater than calves not fed carnitine. This was also statistically significant.

There was also a significantly greater milk replacer intake by the calves fed the Cow's Match™ CMR with carnitine in periods 2 and 3. Total milk replacer intake by calves fed Cow's Match™ with carnitine was approximately 3% greater than calves not fed carnitine. This was also statistically significant.

There was also a significantly greater overall increase in feed efficiency by the calves fed Cow's Match™ with carnitine.

TABLE 1

| Item | | Cow's Match (CMR) | Cow's Match (CMR) w/Carnitine[A] | C.V. |
|---|---|---|---|---|
| No. of Calves | | 17 | 16 | |
| Initial Wt., lbs. | | 107.24 | 107.83 | 2.98 |
| Initial Ig[B] | | 1.76 | 1.90 | 40.53 |
| Avg. Period Gain, lbs. | | | | |
| Period[C] | 1 | 2.78 | 5.39 | 120.48 |
| | 2 | 8.94 | 11.89 | 61.88 |
| | 3 | 10.99[b] | 13.44[a] | 28.72 |
| | 4 | 12.39 | 11.79 | 32.87 |
| | 5 | 12.71 | 14.39 | 35.91 |
| | 6 | 12.26 | 14.00 | 32.81 |
| | 7 | 7.75[b] | 15.48[a] | 46.23 |
| Total | | 67.82[b] | 86.36[a] | 18.44 |
| Avg. Period CMR Consumption, lbs.[D] (DM Basis) | | | | |
| Period[C] | 1 | 10.05 | 10.40 | 12.99 |
| | 2 | 14.35[b] | 15.91[a] | 14.39 |
| | 3 | 16.42[b] | 17.36[a] | 6.04 |
| | 4 | 17.45 | 17.48 | 0.72 |
| | 5 | 17.30 | 17.42 | 2.48 |
| | 6 | 17.17 | 17.47 | 4.22 |
| | 7 | 8.75 | 8.75 | 0.00 |
| Total | | 101.49[b] | 104.79[a] | 3.91 |
| Avg. Period Starter Intake[E], lbs. (DM Basis) | | | | |
| Period[C] | 1 | 0.42 | 0.48 | 151.61 |
| | 2 | 0.94 | 1.16 | 70.87 |
| | 3 | 1.78 | 2.38 | 47.61 |
| | 4 | 2.93 | 3.85 | 41.70 |
| | 5 | 3.31 | 5.34 | 40.07 |
| | 6 | 4.76[b] | 7.72[a] | 40.01 |
| | 7 | 10.82[b] | 17.21[a] | 30.57 |
| Total | | 24.96[b] | 38.14[a] | 33.85 |
| Average Feed Efficiency[F] | | 1.93[b] | 1.67[a] | 12.35 |
| Average Gain: Feed[G] | | 0.52[b] | 0.60[a] | 12.35 |

[A]From L-Carnitine purchased from North American Ingredients, Inc. of Marion, Texas
[B]Gram - % as measured by Zinc Sulfate Turbidity and assigned to 1 of 5 ranges: 0.00-0.49, 0.50-0.99, 1.00-1.49, 1.50-2.49, and 2.50 or higher.
[C]Seven day duration.
[D]Calves were fed 0.9 lbs. CMR/feeding days 1-7, then 1.25 lbs. CMR/feeding days 7-49. CMR twice a day through day 42, then once a day through day 49. Carnitine concentration is 500 mg per kg.
[E]Intense Calf Diet 22 B60, 60 g/ton lasalocid (Land O'Lakes, Inc., Arden Hills, MN).
[F]Average feed efficiency is the amount of feed intake divided by the weight gain of each individual calf. The individual values are summed and then averaged.
[G]Average Gain: Feed is the weight gain of each individual calf divided by the amount of feed intake. The individual values are summed and then averaged.
[a,b]Statistically significant difference (P < 0.05)

The calves fed the Cow's Match™ CMR with carnitine at an enhanced feeding rate showed no significant decrease or increase in severity of scours (scour score), and the number of scour days experienced. There was no statistically significant difference (P>0.05) in average scour scores or days of scouring during the first two weeks of the trial or throughout the entire trial. The scour data is tabulated in Table 2.

TABLE 2

| Item | | Cow's Match (CMR) | Cow's Match (CMR) w/Carnitine[A] | C.V. |
|---|---|---|---|---|
| Avg. Period Scour Score[B] | | | | |
| Period[C] | 1 | 1.89 | 1.71 | 28.89 |
| | 2 | 1.46 | 1.25 | 27.20 |
| | 3 | 1.05 | 1.02 | 9.29 |
| | 4 | 1.00 | 1.00 | 0.00* |
| | 5 | 1.00 | 1.00 | 0.00* |
| | 6 | 1.00 | 1.00 | 0.00* |
| | 7 | 1.00 | 1.00 | 0.00* |

TABLE 2-continued

| Item | | Cow's Match (CMR) | Cow's Match (CMR) w/Carnitine[A] | C.V. |
|---|---|---|---|---|
| | Avg. 2 wk | 1.68 | 1.48 | 23.50 |
| | Avg. 7 wk | 1.20 | 1.14 | 9.29 |
| Avg. Period Scour Days[D] | | | | |
| Period[C] | 1 | 4.59 | 3.69 | 59.17 |
| | 2 | 2.65 | 1.56 | 111.74 |
| | 3 | 0.29 | 0.13 | 414.82 |
| | 4 | 0.00 | 0.00 | 0.00* |
| | 5 | 0.00 | 0.00 | 0.00* |
| | 6 | 0.00 | 0.00 | 0.00* |
| | 7 | 0.00 | 0.00 | 0.00* |
| | Total 2 wk | 7.24 | 5.25 | 64.08 |
| | Total 7 wk | 7.53 | 5.38 | 66.08 |

[A]From L-Carnitine purchased from North American Ingredients, Inc. of Marion, Texas.
[B]Scour Score = 1-4 scale; 1 = normal, 2 = loose, 3 = water separation, 4 = water separation with severe dehydration.
[C]Seven day duration.
[D]Total days with a scour score of 2 or greater
*No differences due to no variations within treatments.

As Table 3 set forth below indicates, a statistically significant reduction in electrolyte costs occurred during period 2 for calves fed the Cow's Match™ CMR with carnitine at an enhanced feeding rate. Although not statistically significant, on an overall basis the calves fed carnitine incurred about 31% less expenses in electrolyte costs than calves that were not fed carnitine.

Calves that were fed the Cow's Match™ CMR with carnitine at an enhanced feeding rate had significant reductions in antibiotic expenses during periods 5 and 7. Calves that were fed the Cow's Match™ CMR with carnitine at the enhanced feeding rate had significant reductions in combined electrolyte and antibiotic expenses during periods 2, 5 and 7. Overall calves fed the Cow's Match™ CMR with carnitine at the enhanced feeding rate had statistically significant reduction in antibiotic expenses and combined electrolyte and antibiotic expenses.

TABLE 3

| Item | | Cow's Match (CMR) | Cow's Match (CMR) w/Carnitine[A] | C.V. |
|---|---|---|---|---|
| Avg. Period Electrolyte Costs, $ | | | | |
| Period[C] | 1 | 5.13 | 4.23 | 68.35 |
| | 2 | 2.84[b] | 1.37[a] | 105.62 |
| | 3 | 0.33 | 0.13 | 351.39 |
| | Total | 8.30 | 5.73 | 70.73 |
| Avg. Period Antibiotic Costs, $ | | | | |
| Period[C] | 1 | 0.39 | 0.16 | 253.37 |
| | 2 | 1.67 | 0.97 | 162.89 |
| | 3 | 0.74 | 1.17 | 177.06 |
| | 4 | 1.30 | 1.20 | 169.85 |
| | 5 | 1.30[b] | 0.36[a] | 175.35 |
| | 6 | 1.28 | 0.64 | 160.81 |
| | 7 | 1.04[b] | 0.18[a] | 227.38 |
| | Total | 7.71[b] | 4.68[a] | 83.10 |
| Avg. Period Electrolyte & Antibiotic Costs, $ | | | | |
| Period[C] | 1 | 5.52 | 4.39 | 67.58 |
| | 2 | 4.51[b] | 2.35[a] | 102.32 |
| | 3 | 1.07 | 1.30 | 154.34 |
| | 4 | 1.30 | 1.20 | 169.85 |
| | 5 | 1.30[b] | 0.36[a] | 175.35 |

TABLE 3-continued

| Item | | Cow's Match (CMR) | Cow's Match (CMR) w/Carnitine[A] | C.V. |
|---|---|---|---|---|
| | 6 | 1.28 | 0.64 | 160.81 |
| | 7 | 1.04[b] | 0.18[a] | 227.38 |
| | Total | 16.01[b] | 10.41[a] | 57.42 |

[A]From L-Carnitine purchased from North American Ingredients, Inc. of Marion, Texas.
[B]Seven day duration.
[a,b]Statistically significant difference (P < 0.05)

The calves fed the Cow's Match™ CMR with carnitine at the enhanced feeding rate showed no overall statistically significant decrease or increase in respiratory scores although the calves that were fed the Cow's Match™ CMR without carnitine at the enhanced feeding rate has statistically significantly better respiratory scores during periods 5 and 6. The respiratory score data is tabulated in Table 4.

TABLE 4

| Item | | Cow's Match (CMR) | Cow's Match (CMR) w/Carnitine[A] | C.V. |
|---|---|---|---|---|
| Avg. Period Respiratory Scores[B] | | | | |
| Period[C] | 1 | 0.24 | 0.00 | 326.21 |
| | 2 | 0.47 | 0.63 | 233.20 |
| | 3 | 0.47 | 1.31 | 206.45 |
| | 4 | 1.29 | 0.88 | 170.65 |
| | 5 | 2.00[b] | 0.44[a] | 152.03 |
| | 6 | 1.59[b] | 0.63[a] | 142.43 |
| | 7 | 0.76 | 0.25 | 232.55 |
| | Total | 6.82 | 4.13 | 92.15 |

[A]From L-Carnitine purchased from North American Ingredients, Inc. of Marion, Texas.
[B]Respiratory scores = 1 respiratory day for each day antibiotic given for respiratory infections.
[C]Seven day duration.
[a,b]Statistically significant difference (P < 0.05)

As indicated in Table 5 below, a statistically significant greater amount of calves fed the Cow's Match™ CMR with the effective amount of carnitine at the enhanced feeding rate were weaned by days 42 and 49 employing the industry criteria as indicated in rows 7 and 8 of Table 4. Specifically, all of the calves fed the Cow's Match™ CMR with the effective amount of carnitine at the enhanced feeding rate could have been weaned by day 49 as compared to 82 percent that were the Cow's Match™ CMR without carnitine at the enhanced feeding rate not fed carnitine employing the LOL Research Farm criteria as indicated in row 4 of Table 5.

TABLE 5

| Item | | | Cow's Match (CMR) | Cow's Match (CMR) w/Carnitine[A] | C.V. |
|---|---|---|---|---|---|
| Avg. Period Weaning Scores[B] | | | | | |
| LOLRF[C] | | 28[E] | 0.12 | 0.19 | 63.45 |
| | | 35[F] | 0.24 | 0.38 | 66.84 |
| | | 42[G] | 0.47 | 0.56 | 58.99 |
| | | 49[H] | 0.82[b] | 1.00[a] | 23.83 |
| IC[D] | | 28[E] | 0.00 | 0.06 | 93.96 |
| | | 35[F] | 0.00 | 0.13 | 73.56 |

TABLE 5-continued

| Item | Cow's Match (CMR) | Cow's Match (CMR) w/Carnitine[A] | C.V. |
|---|---|---|---|
| 42[G] | 0.00[b] | 0.31[a] | 57.39 |
| 49[H] | 0.59[b] | 0.94[a] | 37.96 |

[A]From L-Carnitine purchased from North American Ingredients, Inc. of Marion, Texas.
[B]Weaning Scores = 0-1 scale; 0 = not weaned, 1 = weaned.
[C]Land O' Lakes Research Farm Criteria = calf assumed weaned when 1.0 lb of dry feed consumed for 2 consecutive days.
[D]Industry Criteria = calf assumed weaned when 1.5 lbs dry feed consumed for 3 consecutive days.
[E]Percentage of calves assumed weaned by day 28.
[F]Percentage of calves assumed weaned by day 35.
[G]Percentage of calves assumed weaned by day 42.
[H]Percentage of calves assumed weaned by day 49.
[a,b]Statistically significant difference (P < 0.05)

As Table 6 set forth below indicates, at the end of the 49 day trail calves fed the Cow's Match™ CMR with the effective amount of carnitine at the enhanced feeding rate had a statistically significant increase in hip height, hearth girth, body length and body volume over calves that were fed the Cow's Match™ CMR without carnitine at the effective rate. Overall, calves fed the Cow's Match™ CMR with the effective amount of carnitine at the enhanced feeding rate had a statistically significant increase in hearth girth gain, body length gain and body volume gain over calves that were fed the Cow's Match™ CMR without carnitine at the enhanced feeding rate.

TABLE 6

| Item | | Cow's Match (CMR) | Cow's Match (CMR) w/Carnitine[A] | C.V. |
|---|---|---|---|---|
| Avg. Hip Width, cm | | | | |
| Day | 1 | 17.41 | 17.54 | 2.66 |
| | 49 | 21.14 | 21.31 | 4.80 |
| Avg. Hip Width Gain, cm | | | | |
| Day | 1-49 | 3.74 | 3.77 | 26.04 |
| Avg. Hip Height, cm | | | | |
| Day | 1 | 83.29 | 84.03 | 2.83 |
| | 49 | 91.56[b] | 93.69[a] | 2.75 |
| Avg. Hip Height Gain, cm | | | | |
| Day | 1-49 | 8.26 | 9.66 | 29.52 |
| Avg. Hearth Girth, cm | | | | |
| Day | 1 | 82.53 | 82.38 | 2.26 |
| | 49 | 97.82[b] | 101.00[a] | 2.79 |
| Avg. Hip Height Gain, cm | | | | |
| Day | 1-49 | 15.29[b] | 18.63[a] | 17.18 |
| Avg. Body Length, cm | | | | |
| Day | 1 | 79.82 | 80.13 | 3.22 |
| | 49 | 92.71[b] | 95.56[a] | 3.72 |
| Avg. Body Length Gain, cm | | | | |
| Day | 1-49 | 12.88[b] | 15.44[a] | 24.31 |
| Avg. Body Volume, L[B] | | | | |
| Day | 1 | 174.75 | 176.67 | 4.74 |
| | 49 | 264.79[b] | 288.15[a] | 6.80 |
| Avg. Body Volume Gain, L | | | | |
| Day | 1-49 | 90.04[b] | 111.48[a] | 17.31 |

[A]From L-Carnitine purchased from North American Ingredients, Inc. of Marion, Texas
[B]Body volume = (hearth girth, cm/3.14) × (body length, cm) × (hip height, cm) = (calf volume, cm³/1000) = calf volume, in liters.
[a,b]Statistically significant difference (P < 0.05)

Example 2

A further trial was run to determine what effect of reducing the feeding regimen from an enhanced feeding rate to a conventional feeding rate of milk replacer while maintaining the same concentration of carnitine. Forty (40), three to ten day old Holstein bull calves weighing approximately 90 to 100 pounds were fed a diet of calf milk replacer at the conventional feeding rate. Twenty of the calves were fed milk replacer without carnitine and the other twenty calves were fed milk replacer with carnitine. Two and three calves respectively either died or were so ill that the data relating to these calves was excluded.

Both groups of calves were fed the same amount of the milk replacer under a standard regimen where the calves were fed about 1.25 pounds of milk replacer per day in two feedings of 0.625 pounds per feeding. One group of calves was fed milk replacer supplemented with carnitine at a concentration of 500 milligram per kilogram. Both groups of calves were provided a starter feed that was consumed ad libitum.

The carnitine used in these trials was L-Carnitine purchased from North American Ingredients, Inc. of Marion, Tex. The calf milk replacer (CMR) used was Nursing Formula™ CMR from Land O'Lakes, Inc of Arden Hills, Minn. As Table 7 set forth below shows, there was no statistically significant difference in total weight gain, calf milk replacer consumption, starter feed intake and average feed:gain (feed efficiency) between those calves fed the milk replacer without carnitine and those calves fed 0.284 g per day of carnitine under a standard feed regimen.

TABLE 7

| Item | | Nursing Formula (CMR) | Nursing Formula (CMR) w/Carnitine[A] | P-value | C.V. |
|---|---|---|---|---|---|
| No. of Calves | | 18 | 17 | | |
| Initial Weight, lbs. | | 98.93 | 98.54 | 0.7303 | 3.38 |
| Initial Ig[B] | | 2.94 | 3.41 | 0.2129 | 34.31 |
| Avg. Period Gain, lbs. | | | | | |
| Period[C] | 1 | 0.42 | 0.02 | 0.7622 | 1687.98 |
| | 2 | 3.25 | 3.52 | 0.8423 | 116.79 |
| | 3 | 8.50 | 6.98 | 0.2011 | 44.51 |
| | 4 | 9.96 | 9.47 | 0.7007 | 38.05 |
| | 5 | 14.12 | 13.66 | 0.7087 | 26.17 |
| | 6 | 13.29 | 15.06 | 0.1210 | 23.24 |
| Total | | 49.53 | 48.71 | 0.8509 | 26.29 |
| Avg. Period MR Consumption, lbs. (DM Basis) | | | | | |
| Period[C] | 1 | 6.91 | 6.88 | 0.9077 | 12.48 |
| | 2 | 8.34 | 8.53 | 0.4572 | 9.23 |
| | 3 | 8.75 | 8.75 | 0.0000 | 0.00* |
| | 4 | 8.75 | 8.75 | 0.0000 | 0.00* |
| | 5 | 8.75 | 8.75 | 0.0000 | 0.00* |
| | 6 | 8.75 | 8.75 | 0.0000 | 0.00* |
| Total | | 50.25 | 50.41 | 0.7413 | 2.89 |
| Avg. Period Starter Intake[D], lbs. (DM Basis) | | | | | |
| Period[C] | 1 | 0.37 | 0.35 | 0.9388 | 115.70 |
| | 2 | 1.40 | 1.54 | 0.7098 | 72.37 |
| | 3 | 4.63 | 4.03 | 0.4586 | 54.34 |

TABLE 7-continued

| Item | | Nursing Formula (CMR) | Nursing Formula (CMR) w/Carnitine[A] | P-value | C.V. |
|---|---|---|---|---|---|
| | 4 | 8.74 | 7.03 | 0.2935 | 60.16 |
| | 5 | 12.02 | 11.51 | 0.7127 | 34.47 |
| | 6 | 16.28 | 16.05 | 0.8829 | 28.56 |
| | Total | 43.44 | 40.50 | 0.5778 | 36.72 |
| Average Feed Efficiency[E] | | 1.97 | 1.91 | 0.5324 | 16.25 |

[A]From L-Carnitine purchased from North American Ingredients, Inc. of Marion, Texas.
[B]Gram - % as measured by Zinc Sulfate Turbidity and assigned to 1 of 5 ranges: 0.00-0.49, 0.50-0.99, 1.00-1.49, 1.50-2.49, and 2.50 or higher.
[C]Seven day duration.
[D]Future Cow Starter Bov, 18% Protein, 90 g/ton lasalocid manufactured by Land O'Lakes of Arden Hills, Minnesota.
[E]Average feed efficiency is the amount of feed intake divided by the weight gain of each individual calf. The individual values are summed and then averaged.
*No differences, due to no variation within treatments.

As Table 8 indicates, there was no statistically significant differences between the scour score or scoured days for those calves fed 0.284 g of carnitine per day under a standard feeding regimen and those calves fed under the same regimen with no carnitine.

TABLE 8

| Item | | Nursing Formula (CMR) | Nursing Formula (CMR) w/Carnitine[A] | P-value | C.V. |
|---|---|---|---|---|---|
| | | Avg. Period Scour Score[B] | | | |
| Period[C] | 1 | 1.49 | 1.51 | 0.8697 | 23.15 |
| | 2 | 1.35 | 1.30 | 0.6915 | 25.88 |
| | 3 | 1.06 | 1.02 | 0.1871 | 8.39 |
| | 4 | 1.00 | 1.00 | 0.0000 | 0.00* |
| | 5 | 1.00 | 1.00 | 0.0000 | 0.00* |
| | 6 | 1.00 | 1.00 | 0.0000 | 0.00* |
| | Avg. 2 wk | 1.42 | 1.41 | 0.8863 | 19.67 |
| | Avg. 6 wk | 1.15 | 1.14 | 0.7456 | 8.79 |
| | | Avg. Period Scour Days | | | |
| Period[C] | 1 | 2.89 | 2.88 | 0.9922 | 68.13 |
| | 2 | 2.44 | 2.12 | 0.6899 | 105.04 |
| | 3 | 0.39 | 0.12 | 0.1934 | 234.92 |
| | 4 | 0.00 | 0.00 | 0.0000 | 0.00* |
| | 5 | 0.00 | 0.00 | 0.0000 | 0.00* |
| | 6 | 0.00 | 0.00 | 0.0000 | 0.00* |
| | Total 2 wk | 5.33 | 5.00 | 0.7815 | 68.16 |
| | Total 6 wk | 5.72 | 5.12 | 0.6462 | 71.08 |

[A]From L-Carnitine purchased from North American Ingredients, Inc. of Marion, Texas.
[B]Scour Score = 1-4 scale; 1 = normal, 2 = loose, 3 = water separation, 4 = water separation with severe dehydration.
[C]Seven day duration.
*No differences, due to no variation within treatments.

As Table 9 indicates, there was no statistically significant differences between the total electrolyte cost, total antibiotic cost or combined electrolyte and antibiotic costs for those calves fed 0.284 g of carnitine per day under a standard feeding regimen and those calves fed under the same regimen with no carnitine.

TABLE 9

| Item | | Nursing Formula (CMR) | Nursing Formula (CMR) w/Carnitine[A] | P-value | C.V. |
|---|---|---|---|---|---|
| | | Avg. Period Electrolyte Costs, $ | | | |
| Period[C] | 1 | 0.92 | 0.94 | 0.9227 | 72.57 |
| | 2 | 0.96 | 0.88 | 0.7884 | 96.38 |
| | 3 | 0.20 | 0.10 | 0.3052 | 199.33 |
| | 4 | 0.00 | 0.00 | 0.0000 | 0.00* |
| | Total | 2.08 | 1.92 | 0.7415 | 72.66 |
| | | Avg. Period Antibiotic Costs, $ | | | |
| Period[C] | 1 | 0.63 | 0.72 | 0.8468 | 207.43 |
| | 2 | 1.22 | 1.12 | 0.8482 | 142.77 |
| | 3 | 0.98 | 1.16 | 0.7460 | 155.82 |
| | 4 | 0.88 | 0.81 | 0.8922 | 168.57 |
| | 5 | 0.19 | 0.18 | 0.9365 | 314.46 |
| | 6 | 0.71 | 0.39 | 06258 | 350.35 |
| | Total | 4.61 | 4.38 | 0.8963 | 119.36 |
| | | Avg. Period Electrolyte & Antibiotic Costs, $ | | | |
| Period[C] | 1 | 1.55 | 1.67 | 0.8138 | 88.94 |
| | 2 | 2.18 | 1.99 | 0.7777 | 94.52 |
| | 3 | 1.18 | 1.25 | 0.8932 | 141.50 |
| | 4 | 0.88 | 0.81 | 0.8922 | 168.57 |
| | 5 | 0.19 | 0.18 | 0.9365 | 314.46 |
| | 6 | 0.71 | 0.39 | 0.6258 | 350.35 |
| | Total | 6.69 | 6.29 | 0.8440 | 92.24 |

[A]From L-Carnitine purchased from North American Ingredients, Inc. of Marion, Texas.
[B]Seven day duration.
*No differences, due to no variation within treatments.

As Table 10 set forth below indicates, there was no statistically significant overall difference between respiratory scores for those calves fed 0.284 g per day of carnitine and those calves not fed any carnitine throughout the trial. However, the calves fed carnitine had a statistically significant better respiratory scores during period 4 of the trial.

TABLE 10

| Item | | Nursing Formula (CMR) | Nursing Formula (CMR) w/Carnitine[A] | P-value[D] | C.V. |
|---|---|---|---|---|---|
| | | Avg. Period Respiratory Scores[B] | | | |
| Period[C] | 1 | 0.17 | 0.00 | 0.3386 | 592.11 |
| | 2 | 0.89 | 0.59 | 0.5716 | 209.46 |
| | 3 | 0.89 | 1.00 | 0.8569 | 191.67 |
| | 4 | 1.11 | 0.18 | 0.0489 | 205.62 |
| | 5 | 0.22 | 0.06 | 0.3352 | 345.78 |
| | 6 | 0.50 | 0.18 | 0.3851 | 316.96 |
| | Total | 3.78 | 2.00 | 0.1599 | 125.45 |

[A]From L-Carnitine purchased from North American Ingredients, Inc. of Marion, Texas.
[B]Respiratory scores = 1 respiratory day for each day antibiotic given for respiratory infections.
[C]Seven day duration.
[D]Statistically significant difference for P < 0.05

As Table 11 set forth below indicates, there was no statistically significant overall difference between weaning scores for those calves fed 0.284 g per day of carnitine and those calves not fed any carnitine throughout the trial.

TABLE 11

| Item | | Nursing Formula (CMR) | Nursing Formula (CMR) w/Carnitine[A] | P-value | C.V. |
|---|---|---|---|---|---|
| | | Avg. Period Weaning Scores[B] | | | |
| LOLRF[C] | 27[E] | 0.78 | 0.71 | 0.6387 | 60.39 |
| | 34[F] | 1.00 | 1.00 | 0.000 | 0.00* |
| | 41[G] | 1.00 | 1.00 | 0.000 | 0.00* |
| IC[D] | 27[E] | 0.44 | 0.24 | 0.2036 | 139.08 |
| | 34[F] | 0.83 | 0.76 | 0.6243 | 51.30 |
| | 41[G] | 1.00 | 1.00 | 0.000 | 0.00* |

[A]From L-Carnitine purchased from North American Ingredients, Inc. of Marion, Texas
[B]Weaning Scores = 0-1 scale; 0 = not weaned, 1 = weaned.
[C]Land O'Lakes Research Farm Criteria = calf assumed weaned when 1.0 ob of dry feed consumed for 2 consecutive days.
[D]Industry Criteria = calf assumed weaned when 1.5 lbs dry feed consumed for 3 consecutive days.
[E]Calf assumed weaned by day 27.
[F]Calf assumed weaned by day 34.
[G]Calf assumed weaned by day 41.
*No differences due to no variation within treatments.

Data for parameters presented in the Tables above was analyzed using the general linear model (GLM) statistical procedure of SAS™ Statistical analysis software for a randomized complete block design that included both the particular feed regimen and the week of the test period in the model statement. The SAS™ statistical analysis software is available from SAS Institute, Inc. of Cary, N.C. Additionally, all data was analyzed to determine the mean of the data for each variable under consideration during the collection period for the particular data.

Additionally, the PDiff function of the GLM statistical procedure was used to characterize the mean values of the data by providing for comparisons between mean data values for the calves of different treatments for particular test parameters or variables.

P used in the Tables above is a probability value. For purposes of comparing data in this document, P values of 0.10, or lower, are considered to be statistically significant.

Also, the Tables include a coefficient of variation (CV) for data in a particular row. The coefficient of variation is the standard deviation of a particular variable divided by the mean of the variable and then multiplied by 100.

Although the present invention has been described with reference to preferred embodiments, workers skilled in the art will recognize that changes may be made in form and detail without departing from the spirit and scope of the invention.

What is claimed is:

1. A method of feeding a calf comprising:
   feeding the calf L-carnitine in a milk replacer fed at an enhanced feeding rate such that the calf consumes at least approximately 0.284 grams of carnitine per day.

2. The method of claim 1 wherein the calf consumes more than about 0.55 grams of carnitine per day.

3. The method of claim 1 wherein the L-carnitine is a salt.

4. The method of claim 1 wherein the milk replacer is fed at a rate of more than about 1.25 pounds per day on a dry basis to the calf.

5. The method of claim 1 and wherein the milk replacer is fed at a rate of between about 1.25 pounds per day on a dry basis and about 2.5 weight percent on a dry basis.

6. A method of weaning a calf, the method comprising:
   feeding the calf an effective amount of L-carnitine in a milk replacer in at an enhanced feeding rate such that the calf consumes at least approximately 0.284 grams of carnitine per day.

7. The method of claim 6 wherein the calf consumes about 0.55 grams of carnitine per day.

8. The method of claim 6 wherein the L-carnitine is a salt.

9. The method of claim 6 wherein the milk replacer is fed at a rate of more than about 1.25 pounds per day to the calf.

10. The method of claim 6 the milk replacer is fed at a rate of between about 1.25 pounds per day on a dry basis and about 2.5 weight percent on a dry basis.

11. A method of accelerating growth of a calf, the method comprising:
    feeding the calf an effective amount of L-carnitine in a milk replacer at an enhanced feeding rate such that the rate of growth of the calf is accelerated when compared to a calf fed milk replacer at the enhanced feeding rate without carnitine.

12. The method of claim 11 wherein the calf consumes more than 0.284 grams of carnitine per day.

13. The method of claim 11 wherein the calf consumes more than about 0.55 grams of carnitine per day.

14. The method of claim 11 wherein the L-carnitine is a salt.

15. The method of claim 11 wherein the milk replacer is fed at a rate of more than 1.25 pounds per day to the calf.

16. The method of claim 11 the milk replacer is fed at a rate of between about 1.25 pounds per day on a dry basis and about 2.5 weight percent on a dry basis.

* * * * *

UNITED STATES PATENT AND TRADEMARK OFFICE
CERTIFICATE OF CORRECTION

PATENT NO.       : 7,955,629 B2                                 Page 1 of 1
APPLICATION NO.  : 12/346209
DATED            : June 7, 2011
INVENTOR(S)      : Miller It is certified that error appears in the above-identified patent and that said Letters Patent is hereby corrected as shown below:

SPECIFICATION

| Column | Line | PTO | Should Read |
| --- | --- | --- | --- |
| 1 | 19 | "camitine" | -- carnitine -- |
| 1 | 41 | "camitine" | -- carnitine -- |
| 1 | 43 | "camitine" | -- carnitine -- |
| 1 | 46 | "camitine" | -- carnitine -- |
| 1 | 54 | "camitine" | -- carnitine -- |
| 1 | 56 | "camitine" | -- carnitine -- |
| 1 | 65 | "camitine" | -- carnitine -- |
| 8 | 11 | "camitine" | -- carnitine -- |
| 8 | 19 | "camitine" | -- carnitine -- |

Signed and Sealed this
Thirteenth Day of September, 2011

David J. Kappos
*Director of the United States Patent and Trademark Office*